(12) United States Patent
Mizutani et al.

(10) Patent No.: US 6,500,160 B2
(45) Date of Patent: Dec. 31, 2002

(54) PACKAGE FOR ABSORBENT ARTICLE

(75) Inventors: Satoshi Mizutani, Kagawa (JP); Makoto Suekane, Kagawa (JP); Junichi Noguchi, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 09/883,972

(22) Filed: Jun. 19, 2001

(65) Prior Publication Data

US 2001/0056270 A1 Dec. 27, 2001

(30) Foreign Application Priority Data

Jun. 19, 2000 (JP) ............................... 2000-182864

(51) Int. Cl.$^7$ ............................................. A61F 13/20
(52) U.S. Cl. ................................. 604/385.02; 206/440
(58) Field of Search ...................... 604/385.02–385.05; 206/440

(56) References Cited

U.S. PATENT DOCUMENTS

| | | | | |
|---|---|---|---|---|
| 6,036,679 A | * | 3/2000 | Balzar et al. | 206/438 |
| 6,312,418 B1 | * | 11/2001 | Shimizu et al. | 604/385.02 |
| 6,380,455 B1 | * | 4/2002 | Moder et al. | 206/440 |
| 6,402,727 B1 | * | 6/2002 | Rosengrant | 206/440 |

* cited by examiner

*Primary Examiner*—Glenn K. Dawson
*Assistant Examiner*—C L Anderson
(74) *Attorney, Agent, or Firm*—Darby & Darby

(57) ABSTRACT

Disclosed is a package including an absorbent article and a packaging member. The packaging member is formed of a nonwoven fabric composed of thermoplastic fibers. The nonwoven fabric has a plurality of heat-fused portions arranged thereon in a predetermined pattern. The heat-fused portions are formed by pressing and heat-fusing the nonwoven fabric. The nonwoven fabric has a tensile strength of from 4.5 to 20 N/25 mm in MD and from 4.5 to 15 N/25 mm in CD and has a breathability resistance of at least 0.04 kPa-s/m.

15 Claims, 4 Drawing Sheets

FIG. 5 Water resistance measuring apparatus (for low water pressure)
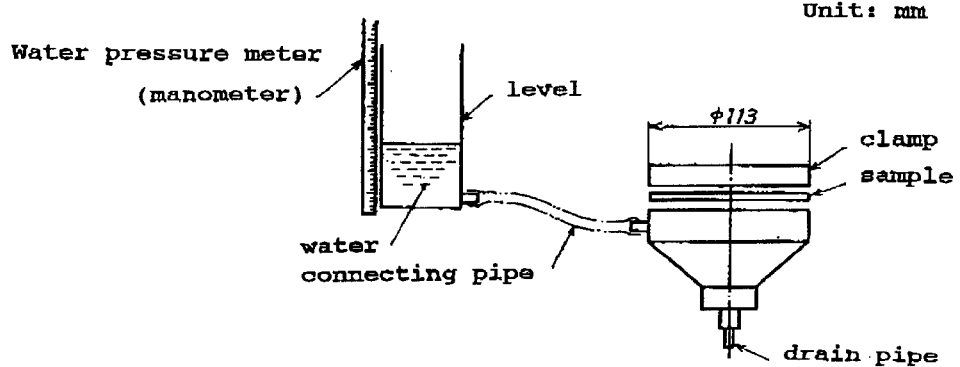
FIG. 6 Cantilever type tester
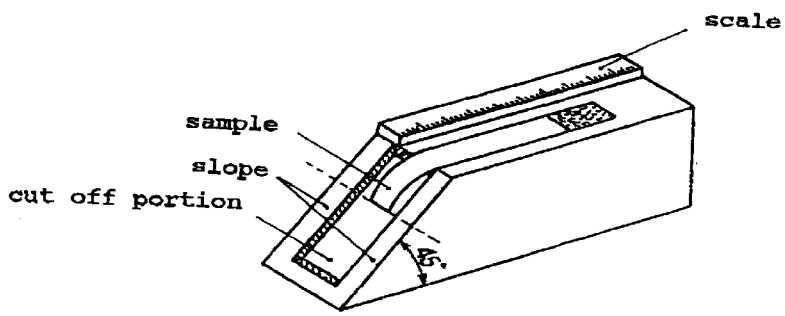

PACKAGE FOR ABSORBENT ARTICLE

BACKGROUND OF THE INVENTION

1. Field of the Invention

The present invention relates to a package for an absorbent article, in which an absorbent article such as sanitary napkin, panti-liner or the like is individually packaged.

2. Related Art

Absorbent article such as sanitary napkins, panti-liners or the like are individually packaged with packaging members. When the individually packaged absorbent article is to be used, its packaging member is unsealed and the absorbent article is taken out and worn. At this time, a used absorbent article replaced by the new one can be disposed of while being wrapped in the packaging member thus unsealed for taking out the new one.

When absorbent articles are individually packaged, the packaging member is demanded to have barrier properties so that dust or moisture in the atmosphere at a storage place may not be infiltrated before use through the packaging member to stick to the inside absorbent article. Because of this demand for the barrier properties, most of the packaging members used in the prior art are made of a synthetic resin film.

However, in the case where the packaging member is made of a synthetic resin film, there is a defect that the film causes zipping sound or rustling sound when the package is unsealed, to thereby make the user mentally uncomfortable. Especially since the film is strongly sealed at its edge portions so as to keep cleanliness inside of the package, zipping sound becomes loud when these sealed portions are separated. In addition, the packaging member formed of a synthetic resin film looks poor in softness and does not provide a good appearance.

In the case where the packaging member is formed of a nonwoven fabric, on the other hand, it can provide a soft appearance. Moreover, the nonwoven fabric per se is soft and is effective for suppressing zipping sound at the unsealing time. Since the nonwoven fabric is an aggregate of fibers, however, fine dust in the atmosphere may be infiltrated through the packaging member to stick to the inside absorbent article thereby to cause a hygienic problem.

In addition, the absorbent article such as sanitary napkin is generally provided on its back sheet with pressure-sensitive adhesive layers for adhering to shorts or the like in use, and therefore, the packaging member is provided with release sheets for protecting the pressure-sensitive adhesive layers until use. These release sheets should be firmly adhered and secured onto the packaging member. However, if the nonwoven fabric is formed of fibers opened by a carding process, the fibers on the surface of the nonwoven fabric are liable to fluff. Accordingly, it is difficult to firmly adhere and secure the release sheets onto the packaging member of the nonwoven fabric. For this difficulty, the release sheets may be caused to leave the packaging member by the separating force which is established when the absorbent article is separated from the release sheets.

Further, the ordinary packaging member is provided at its one edge with a tap tape. When the packaging member is folded together with the absorbent article, this tab tape adheres to the outer face of the underlying portion of the packaging member, thereby to complete the package. When the absorbent article after use is to be wrapped in the packaging member, then, the tab tape adheres to the outer face of the packaging member so that the wrapped state can be maintained. However, if the surface of the nonwoven fabric forming the packaging member is liable to fluff, part of fluffed fibers easily drop and stick to the pressure-sensitive adhesive layer of the tab tape, thereby to lower the adhesion (or tack) of the tab tape for repetitive use. As a result, when the absorbent article after use is to be wrapped in the packaging member, there arises a problem that the packaging member cannot be reliably maintained in the wrapped state.

Furthermore, since the nonwoven fabric is soft, there also arises a problem that when the absorbent article is separated from the release sheets, the nonwoven fabric is easily folded or curled to unintentionally stick to the pressure-sensitive adhesive layers of the absorbent article. It may then take a time to wear the absorbent article. At this time, if the fluffed fibers on the surface of the nonwoven fabric drop and stick to the pressure-sensitive adhesive layers of the absorbent article, the adhesion (or tack) of these pressure-sensitive adhesive layers is lowered. As a result, the adhesion of the absorbent article to the shorts or the like becomes weak.

SUMMARY OF THE INVENTION

The present invention has an object to provide a package which is excellent in barrier properties against dust or moisture and which is soft and reluctant to cause zipping sound at the unsealing time.

According to a first aspect of the invention, there is provided a package comprising an absorbent article and a packaging member, the absorbent article including: a back sheet; a liquid-permeable top sheet; and an absorbent layer sandwiched between the back sheet and the top sheet, and being folded and packaged with the packaging member, confronting faces of each side edge region of the packaging member being joined to each other outside of the absorbent article, wherein the packaging member is formed of a nonwoven fabric composed of thermoplastic fibers, the nonwoven fabric having a plurality of heat-fused portions arranged thereon in a predetermined pattern, the heat-fused portions being formed by pressing and heat-fusing the nonwoven fabric, wherein the nonwoven fabric has a tensile strength of from 4.5 to 20 N/25 mm in MD and from 4.5 to 15 N/25 mm in CD and has a breathability resistance of at least 0.04 kPa·s/m.

The packaging member according to the first aspect of the invention is formed of the nonwoven fabric so that it causes less zipping or rustling sound when unsealed, especially when the joined portions of the packaging member are separated. Because of the plurality of heat-fused portions, moreover, the breathability resistance can be enhanced to make fine dust in the atmosphere reluctant to enter the inside of the packaging member.

According to a second aspect of the invention, there is provided a package comprising an absorbent article and a packaging member, the absorbent article including: a back sheet; a liquid-permeable top sheet; and an absorbent layer sandwiched between the back sheet and the top sheet, and being folded and packaged with the packaging member, confronting faces of each side edge region of the packaging member being joined to each other outside of the absorbent article, wherein the packaging member includes: an inner face layer confronting the back sheet of the absorbent article; an outer face layer directed outward of the package; and an intermediate layer sandwiched between the inner face layer and the outer face layer, the intermediate layer being formed of a melt-blown nonwoven fabric composed of thermoplastic micro fibers, the inner face layer and the outer face layer being formed of a spun-bonded nonwoven fabric composed of continuous thermoplastic filaments, wherein the inner face layer, the intermediate layer and the outer face layer are heat-fused to one another.

In the package according to the second aspect of the invention, it is desirable that the packaging member has a breathability resistance of at least 0.04 kPa-s/m. It is also desirable that the packaging member has a plurality of heat-fused portions arranged thereon in a predetermined pattern, and the heat-fused portions are formed by pressing and heat-fusing the inner face layer, the intermediate layer and the outer face layer.

In the packaging member according to the second aspect of the invention, the intermediate layer is formed of the melt-blown nonwoven fabric composed of micro fibers. This melt-blown nonwoven fabric has high barrier properties against fine dust or moisture in the atmosphere because of its high fiber density, so that the absorbent article packaged with the packaging member can be kept clean. Because the packaging member is made of the nonwoven fabrics, moreover, zipping or rustling sound is hardly caused at the unsealing time. By forming the plurality of heat-fused portions, moreover, the breathability resistance can be easily enhanced.

In both the first and second aspects of the invention, the breathability resistance can be easily set to at least 0.04 kPa-s/m, if each heat-fused portion has an area of from 0.07 to 0.28 $mm^2$, and if the area ratio of the heat-fused portions to the packaging member is from 10 to 30%.

Preferably, the water resistance of the packaging member is at least 80 $mmH_2O$ according to JIS L-1092 (Method A: a low water pressure method).

Preferably, the bending resistance of the packaging member is from 30 to 70 mm at an average value of MD and CD according to JIS L-1018 (a cantilever method). If the bending resistance is within this range (i.e., if the packaging member has a proper rigidity), the packaging member having a soft appearance can be easily unsealed while retaining its shape.

Preferably, a pressure-sensitive adhesive layer is disposed on the back sheet of the absorbent article, and a release sheet, to which the pressure-sensitive adhesive layer is to be adhered, is fixed on an inner face of the packaging member, at a portion to confront the back sheet of the absorbent article.

According to the first and second aspects of the invention, the nonwoven fabric forming the packaging member is formed with the plurality of heat-fused portions or the back layer for confronting the absorbent article is formed of the spun-bonded nonwoven fabric composed of continuous fibers. Therefore, the packaging member has such a high surface strength as to prevent dropping of fibers from the surface. Therefore, the release sheet can be firmly adhered and fixed on the inner face of the packaging member, so that the release sheet is hardly separated from the inner face of the packaging member when the pressure-sensitive adhesive layer of the absorbent article is peeled off from the release sheet.

Preferably, the bending resistance of the release sheet is from 50 to 120 mm at an average value of MD and CD according to JIS L-1018 (a cantilever method).

Preferably, the packaging member is folded together with the absorbent article to have two portions, one overlying the other, the overlying portion has one end edge of the packaging member which is not directly joined to the underlying portion, a tab tape is fixed on an outer face of the overlying portion of the packaging member, and has a portion protruding from the end edge, and the protruding portion is provided with a pressure-sensitive adhesive layer which is adhered to an outer face of the underlying portion of the packaging member.

More preferably, the region to which the pressure-sensitive adhesive layer of the tab tape is adhered, contains the heat-fused portions.

If the outer face layer of the packaging member is formed of the spun-bonded nonwoven fabric and/or if the surface of the packaging member is formed with the plurality of heat-fused portions, the fibers on the surface of the packaging member are prevented from fluffing. Therefore, even after the tab tape is once peeled off, its adhesion (or tack) is not lowered, thereby to enable the repetitive adhesion.

BRIEF DESCRIPTION OF THE DRAWINGS

FIG. 5 is an illustration of a measuring apparatus (for low water pressure); and FIG. 6 is an illustration of a cantilever type tester.

DESCRIPTION OF THE PREFERRED EMBODIMENT

Figure 1:
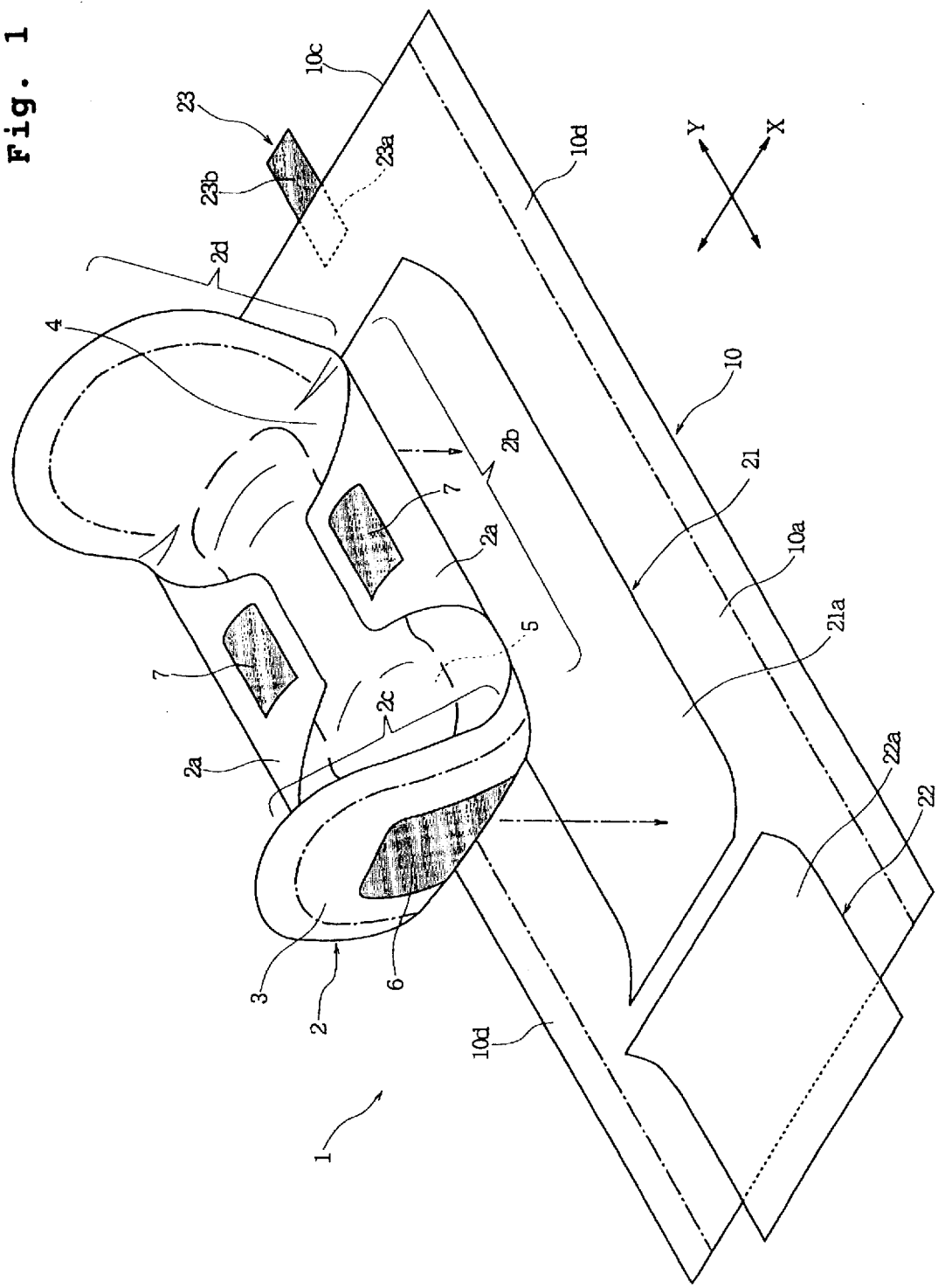
FIG. 1 is a perspective view showing the unsealed state of a package for an absorbent article according to one embodiment of the invention.
Figure 2:
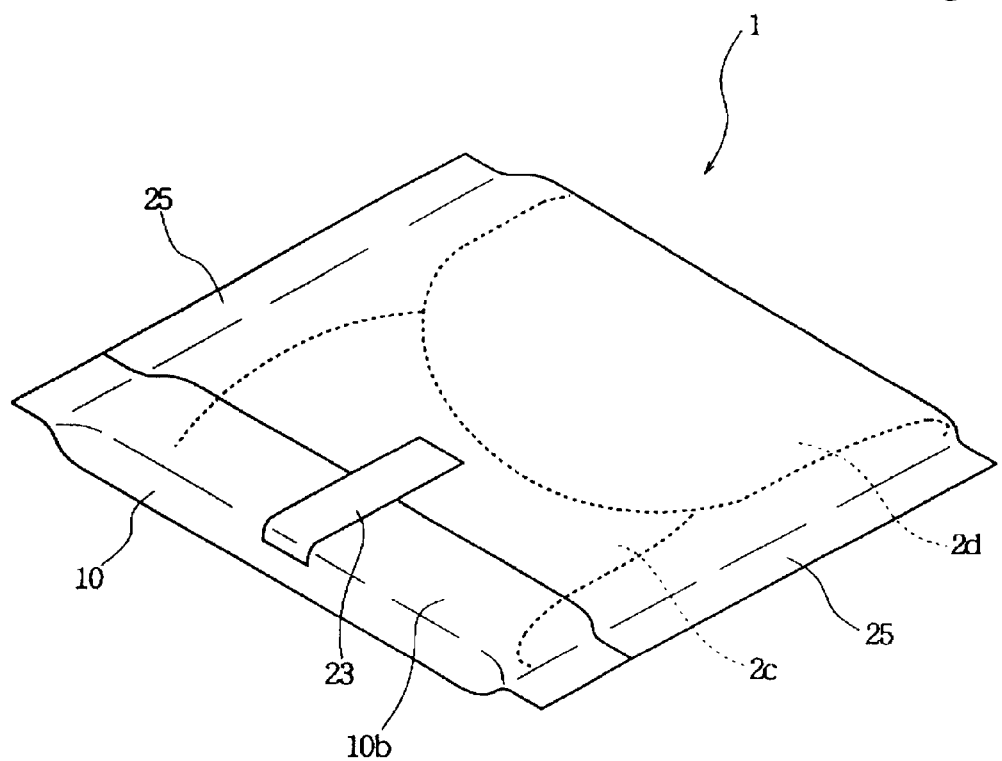
FIG. 2 is a perspective view showing the sealed state of the package of FIG. 1.
Figure 3:
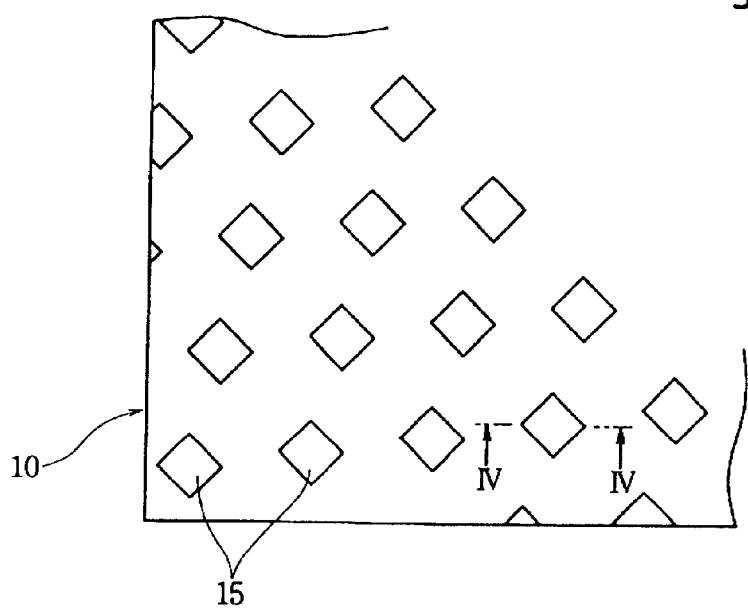
FIG. 3 is an enlarged top plan view showing a portion of a packaging member.
Figure 4:
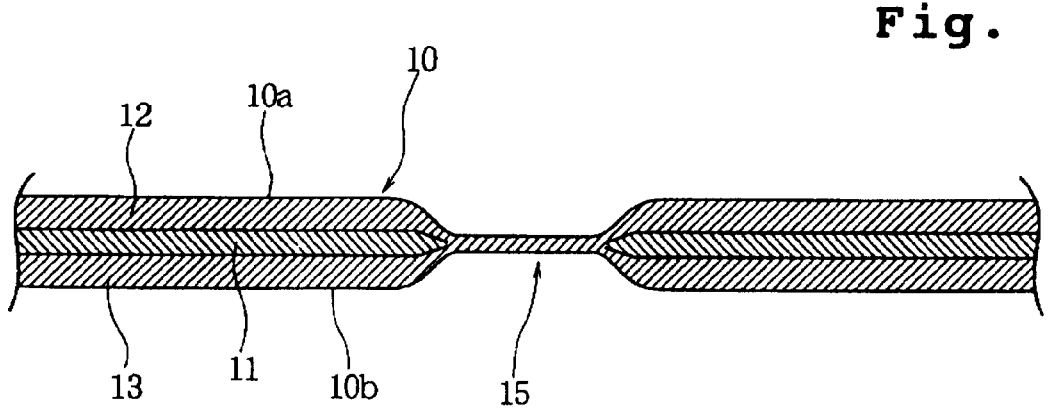
FIG. 4 is an enlarged sectional view of a portion taken along line IV—IV of FIG. 3.

FIG. 1 is a perspective view showing the unsealed state of a package for an absorbent article according to one embodiment of the invention; FIG. 2 is a perspective view showing the sealed state of the package of FIG. 1, in which the absorbent article (partially shown by dotted line) is packaged by a packaging member; FIG. 3 is an enlarged top plan view showing a portion of the packaging member of FIGS. 1 and 2; and FIG. 4 is an enlarged sectional view of a portion taken along line IV—IV of FIG. 3.

As used herein, the term "absorbent article" refers to devices which absorb and contain body exudates, and more specifically, refers to devices which are placed against the skin of a wearer to absorb and contain the various exudates discharged from the body. Hereinafter, the absorbent article is shown embodied in a sanitary napkin. However, it should be noted that the present invention is also applicable to any absorbent articles, such as panti-liners or the like.

In the embodiment shown in FIGS. 1 and 2, a package is generally indicated at 1. The package 1 comprises a packaging member 10 and a sanitary napkin 2 individually packaged with the packaging member 10.

The sanitary napkin 2 is constructed to include: a liquid-impermeable back sheet 3; a liquid-permeable top sheet 4; and an absorbent layer 5 sandwiched between the back sheet 3 and the top sheet 4. These back sheet 3 and top sheet 4 are joined to each other around the absorbent layer 5. The sanitary napkin 2 has: a main body composed of a central portion 2b, a front portion 2c and a rear portion 2d; and wing portions 2a and 2a protruded from the central portion 2b to the right and left sides in X-direction. These wing portions 2a and 2a are formed of the portions where the back sheet 3 and the top sheet 4 are joined to each other.

On the surface of the back sheet 3, there are separately disposed three (3) pressure-sensitive adhesive layers. These pressure-sensitive adhesive layers are made of elastomer such as synthetic resin or synthetic rubber so that they can exhibit proper adhesion (or tack) repeatedly for the object to be adhered (e.g., shorts). Specifically, one pressure-sensitive adhesive layer 6 is positioned in the area of the back sheet 3 forming the main body of the sanitary napkin 2; and two pressure-sensitive adhesive layers 7 and 7 are positioned in the areas of the back sheet 3 forming the wing portions 2a and 2a respectively. The pressure-sensitive adhesive layer 6 is located general at the center of the main body in the transverse direction (X-direction) of the sanitary napkin 2 and extended in the longitudinal direction (Y-direction) of the sanitary napkin 2 to range from the central portion 2b to generally midway positions of the front portion 2c and the rear portion 2d.

When this sanitary napkin 2 is applied to shorts, for example, the pressure-sensitive adhesive layer 6 on the main body is adhered to the inner face of the crotch portion of the shorts, and the wing portions 2a and 2a are folded back to make the pressure-sensitive adhesive layers 7 and 7 adhere to the outer face of the crotch portion of the shorts.

The packaging member 10 is formed of a composite nonwoven fabric. This packaging member 10 is made softer than a synthetic resin film and hardly causes zipping sound (i.e., rustling sound) when unsealed. In addition, the packaging member 10 is highly resistant to water and air-permeation so that it can prevent fine dust or moisture in the atmosphere from passing through it. Therefore, the inside of the resulting package 1 is well isolated from the outside. Moreover, the packaging member 10 has inner and outer faces that hardly fluff (or fuzz). Still moreover, since the packaging member 10 has a moderate rigidity, it is not unintentionally curled or folded when it is unsealed for taking out a sanitary napkin or when it is used for wrapping a used sanitary napkin. Therefore, the packaging member 10 can be prevented from being unintentionally adhered to the pressure-sensitive adhesive layers 6 or 7.

As shown in the sectional view of FIG. 4, the packaging member 10 is made of a composite nonwoven fabric composed of an intermediate layer 11, an inner face layer 12 forming an inner face 10a of the packaging member 10, and an outer face layer 13 forming an outer face 10b of the packaging member 10.

The intermediate layer 11 is formed of a melt-blown nonwoven fabric. This melt-blown nonwoven fabric is prepared by extruding a molten thermoplastic resin from the fine nozzles of a spinner while blowing out hot air from around the fine nozzles to form continuous micro fibers and by heat-fusing the continuous micro fibers with a heat roller or the like. Examples of the thermoplastic micro fibers include: mono-fibers of PE (polyethylene), PP (polypropylene) or PET (polyethylene terephthalate); fibers of graft polymer of PE and PP; and conjugated fibers of a core-sheath structure having a core of PP or PET and a sheath of PE. The melt-blown nonwoven fabric thus formed of the micro fibers has a high fiber density and a low porosity (or void volume) so that it is excellent in barrier properties against the dust in the atmosphere and resistance to water. Moreover, the melt-blown nonwoven fabric is so soft that it hardly generates rustling sound unlike a resin film.

The micro fibers forming the melt-blown nonwoven fabric are preferred to have a fineness of from 0.11 to 0.66 dtex. If the fineness is less than this range, the fibers are easily cut when spun by the spinner, so that they are not homogeneously dispersed in the nonwoven fabric to form a coarse region of a low fiber density thereby to make the barrier function unstable. If more than the range, the fiber density is lowered in the entire area of the nonwoven fabric so that the nonwoven fabric becomes inferior in the barrier properties and the water resistance.

The intermediate layer 11 of the melt-blown nonwoven fabric is preferred to have a basis weight of from 3 to 20 $g/m^2$. If less than this range, the intermediate layer 11 becomes too thin to have excellent barrier properties and water resistance, and the packaging member 10 is degraded in rigidity and strength.

Both the inner face layer 12 and the outer face layer 13 are formed of a spun-bonded nonwoven fabric. This spun-bonded nonwoven fabric is prepared by extruding a molten thermoplastic resin from the nozzles of a spinner to form continuous fibers (filaments) and by heat-fusing the continuous fibers between heat rollers. Therefore, the spun-bonded nonwoven fabric is soft in its entirety so that it hardly generates zipping sound unlike a rigid film. Since the continuous fibers are heat-fused, moreover, the spun-bonded nonwoven fabric has a higher surface strength and is highly resistant to fluffing on its surface, as compared with a nonwoven fabric in which fibers formed into a web by a carding process are bonded. Still moreover, the spun-bonded nonwoven fabric is highly resistant to layer peeling force (or ply separation force) in the thickness direction. Therefore, the release sheet and tab tape, as will be described hereinafter, can be easily adhered thereto. In addition, the pressure-sensitive adhesive layers 6 and 7 of the sanitary napkin 2 or a pressure-sensitive adhesive layer of the tab tape having been adhered thereto can be easily peeled with little fluff, so that the adhesion (or tack) of the pressure-sensitive adhesive layers is hardly lowered.

Examples of the continuous thermoplastic fibers include: fibers of PE, PP, PET or a graft polymer of PE and PP; or conjugated fibers of a core-sheath structure having a core of PP or PET and a sheath of PE. The continuous fibers forming the spun-bonded nonwoven fabric are preferred to have a fineness of from 1.1 to 5.5 dtex. If more than this range, the pressure-sensitive adhesive easily infiltrates the inner face layer 12 or the outer face layer 13 to stick to the intermediate layer 11 when the pressure-sensitive adhesive layers 6 and 7 of the sanitary napkin 2 or the pressure-sensitive adhesive layer of the tab tape contacts the inner face layer 12 or the outer face layer 13. The melt-blown nonwoven fabric forming the intermediate layer 11 has a lower strength than that of the spun-bonded nonwoven fabric forming the inner face layer 12 and the outer face layer 13. Therefore, if the pressure-sensitive adhesive layer sticks to the intermediate layer 11 through the layer 12 or 13 and is then peeled therefrom, the packaging member 10 is liable to break. If the fineness is less than that range, on the other hand, the strength of the spun-bonded nonwoven fabric becomes so low that the adhesion of the release sheet or the tab tape is easily weakened by the falling-out of fibers.

The spun-bonded nonwoven fabric is preferred to have a basis weight of from 5 to 15 $g/m^2$. If less than this range, the strength of the packaging member 10 is lowered against the pressure-sensitive adhesive layers.

As shown in FIGS. 3 and 4, the melt-blown nonwoven fabric for forming the intermediate layer 11 and the spun-bonded nonwoven fabrics for forming the inner face layer 12 and the outer face layer 13 are pressed and heated in a laminated state by a predetermined emboss pattern to form partially heat-fused portions 15, by which the individual layers are joined to one another. These partially heat-fused portions 15 can be formed by feeding the three layers of nonwoven fabrics between an emboss roller having protrusions of a predetermined pattern and a roller having a smooth surface, and by heating and pressing them with the rollers.

Since the packaging member 10 is constructed of the three layers of nonwoven fabrics and is fused by pressing and heating them at the partially heat-fused portions 15, as shown in FIG. 3, the overall rigidity of the packaging member 10 can be kept at a proper level for causing no rustling sound unlike films and for being prevented from being curled when unsealed. With the partially heat-fused portions 15 being thus formed, moreover, it is possible to enhance the tensile strength (or breaking strength) of the packaging member 10. With the partially heat-fused portions 15, still moreover, the packaging member 10 may be highly resistant to water and air-permeation, as will be described hereinafter. The resistance to water and the resistance to air-permeation are referred to as "water resistance" and "breathability resistance", respectively.

In order to set the rigidity, the strength, the water resistance and the breathability resistance to desired values, the individual partially heat-fused portions 15 are preferred to have the maximum width of from 0.3 to 0.6 mm and an area ranging from 0.07 to 0.28 mm$^2$. More preferably, the maximum width is from 0.3 to 0.4 mm, and the area is from 0.07 to 0.12 mm$^2$. It is also preferred that the area ratio of the partially heat-fused portions 15 to the packaging member 10 is in a range from 10 to 30%.

The packaging member 10 having the three-layered structure is preferred to have a water resistance of at least 80 mm H$_2$O (or a water level of 80 mm) according to JIS (Japanese Industrial Standard) L-1092 (Method A: a low water pressure method). Here, (1) Method A (low water-pressure method) is performed as follows:

(1.1) Apparatus and material: following apparatus and material are used.
   (a) Water resistance measuring apparatus (for low water pressure) is an apparatus shown in FIG. 5, in which a level can rise at a speed of 60±3 cm/min and 10±0.5 cm/min. On the other hand, a clamp is sized to make a sample come into contact with water at 100 cm$^2$.
   (b) Water pressure meter (Manometer) graduated in 0.5 cm, and having the highest high-water level of about 1 to 2 m when the level rises.
   (c) Stop watch graduated in 0.5 sec.
   (d) Measuring cylinder graduated in ml.
   (e) Water: distilled water or ion-exchanged water is used. A temperature is set at 20±2° C. in principal at the time of testing; if not, the temperature should be noted.

(1.2) Operation: four pieces of sample material having a size of about 15×15 cm are cut out for following tests, respectively. They are attached to the water resistance measuring apparatus of FIG. 5 so that water comes into contact from the front side, i.e., the side with which water comes into contact during use of the sample. By raising the level containing the water at the speed of 60±3 cm/min or 10±0.5 cm/min, the water resistance is measured in accordance with any of the following methods. The test is repeated 4 times and averaged to the first decimal place. The method employed should be noted.

(a) Hydrostatic pressure method
      Water level when water comes out from three positions on the back side, is measured down to 0.5 cm, as the water level rises. However, in the case where water does not come out from three positions even though the water level rises, the water level when water comes out from one or two positions is measured. This should be indicated.
      Here, a very small drop of water which does not grow larger after coming out should not be taken into account.

In accordance with the invention, a breathability resistance tester (i.e., a textile air permeability tester) manufactured by Kato Tech and having a model number of KES F8 AP1 is used.

With the partially heat-fused portions 15 being thus formed, moreover, the tensile strength (or the breaking strength) of the nonwoven fabric can be set at from 4.5 to 20 N/25 mm in MD and at from 4.5 to 15 N/25 mm in CD so that it is sufficient for the use as the packaging member.

Here, the packaging member of the invention should not be limited to the aforementioned three-layered structure, so long as the inner face and the outer face are formed of the spun-bonded nonwoven fabric and at least one layer of the melt-blown nonwoven fabric is present between them. That is, the packaging member may have a laminated structure of four, five or more layers.

Moreover, other kinds of nonwoven fabrics may be employed for forming the packaging member of the invention in place of the melt-blown nonwoven fabric or the spun-bonded nonwoven fabric, so long as they can realize the strength, the water resistance and the breathability resistance required in the invention by forming such partially heat-fused portions as described in the embodiment.

On the inner face 10a of the packaging member 10, as shown in FIG. 1, there are fixed a first release sheet 21 and a second release sheet 22. These two release sheets 21 and 22 are formed of a synthetic resin film, a thin paper, a laminate in which a film is laminated on a paper or nonwoven fabric, or the like. A silicone or a fluorine resin is applied to the surfaces 21a and 22a of the individual release sheets 21 and 22 to provide a heat-cured, UV cured or EB treated release face so that the release sheets 21 and 22 can be repeatedly peeled from and adhered to the pressure-sensitive adhesive layers 6 and 7 of the absorbent article.

The release sheets 21 and 22 are fixed with an adhesive on the inner face 10a of the packaging member 10, i.e., on the surface of the inner face layer 12 of a spun-bonded nonwoven fabric. The adhesive sticks, if excessively applied, to the melt-blown nonwoven fabric of the intermediate layer 11. Therefore, it may break the intermediate layer 11 when the peeling force acts on the release sheets 21 and 22. If a heat-hardening adhesive is used and pressed with heat rolls, on the other hand, the thermoplastic fibers of the melt-blown nonwoven fabric may fuse to degrade the barrier properties of the intermediate layer 11.

Therefore, the adhesive for adhering the release sheets 21 and 22 to the inner face 10a of the packaging member 10 is preferably exemplified by a pressure-sensitive adhesive of synthetic rubber or the like. For the adhesion, this adhesive is preferably applied with a low basis weight and pressed with rollers at the room temperature. Here, the adhesion peeling strength between the release sheets 21 and 22 and the packaging member 10 is preferably from 490 to 3920 mN/cm$^2$.

On one end edge (or shorter side) 10c of the packaging member 10, there is fixed a tab tape 23. This tab tape 23 has an adhesive portion 23a and 23b. The adhesive portion 23a is applied with a pressure-sensitive adhesive similar to that of the release sheets 21 and 22 and is adhered and fixed on the outer face 10b of the packaging member 10. On the other hand, the adhesive portion 23b protruding from the end edge 10c is formed with a different kind of pressure-sensitive adhesive layer having a weaker adhesion (or tack) than that of the adhesive portion 23a, so that it can be repeatedly peeled and adhered.

The rigidity of the packaging member 10 is increased in the area to which the release sheets 21 and 22 are adhered. That is, the packaging member 10 has a high rigidity region to which the release sheets 21 and 22 are adhered; and a low rigidity region to which the release sheets 21 and 22 are not adhered.

The low rigidity region (i.e., the region to which the release sheets 21 and 22 are not adhered) is preferred to have a rigidity (or bending resistance) of from 30 to 70 mm according to JIS L-1018 (using the cantilever method). In this case, 6.22.1 Method A (45° cantilever method). Here, five pieces of samples having a size of 2× about 15 cm are cut out along the wale direction and course direction, respectively. It is placed on a smooth surfaced horizontal table having a slope of 45° on one end thereof, as shown in FIG. 6, with its one shorter side being set at the base line of the scale. The sample is then gently slid toward the slope by an appropriate manner. When one edge of the sample comes into contact at its midpoint with the slope A, the position of the other edge is read by the scale. The bending resistance is expressed as the distance (mm) over which the sample is moved. The five pieces of sample are measured for both front and back faces and values are averaged (down to integral places) in the wale direction and course direction, respectively. The package 1 hardly keeps its shape, if the rigidity is less than that range, but easily causes zipping sound if more than the range.

On the other hand, the release sheets 21 and 22 forming the high rigidity region are preferred to have a rigidity (or bending resistance) of from 50 to 120 mm. In addition, the area ratio of the high rigidity region to the packaging member 10 is preferably from 20 to 70%. It is further preferred that the ratio of the width of the high rigidity region to that of the packaging member 10 in the end edge direction (i.e., the X-direction) is from 40 to 70%.

In order to form the high rigidity region, it is preferred that the rigidity of the release sheets is higher by 1.6 to 4 times than that of the nonwoven fabric forming the packaging member 10.

With this high rigidity region, the package 1 can easily keep its shape shown in FIG. 2 and is prevented from being unintentionally curled or folded when unsealed or used for packaging a used sanitary napkin, so that it can prevent the nonwoven fabric of the packaging member 10 from being directly adhered to the pressure-sensitive adhesive layers 6 and 7 of the sanitary napkin 2. Since the release sheets 21 and 22 are highly rigid, moreover, the release sheets can be felt and located by the hands of a wearer when the package is to be unsealed. Therefore, even when the nonwoven fabric and the release sheets have an identical color or even when the sanitary napkin is to be worn in the dark, the release sheets can be easily located.

The package 1 shown in FIG. 2 is formed as following. First, the pressure-sensitive adhesive layer 6 disposed on the main body area of the back sheet 3 of the sanitary napkin 2 is adhered to the surface 21a of the first release sheet 21 fixed on the inner face 10a of the packaging member 10, as shown in FIG. 1. Then, the front portion 2c of the sanitary napkin 2 is covered with a portion of the second release sheet 22 that is not adhered to the packaging member 10, so that when the front portion 2c is folded back together with a portion of the packaging member 10 onto the central portion 2b, the surface 22a of the second release sheet 22 is adhered to the pressure-sensitive adhesive layers 7 and 7 disposed on the wing portions 2a and 2a of sanitary napkin 2, while preventing the front portion 2c from adhering to the adhesive layers 7 and 7. Thereafter, the rear portion 2d of the sanitary napkin 2 is folded back together with a portion of the packaging member 10 and is laid on the folded front portion 2c.

In such a folded state, confronting faces of each side edge region 10d of the packaging member 10 are fused to each other by using a heat roll to thereby form sealed portions 25 and 25, as shown in FIG. 2. In addition, the adhesive portion 23b of the tab tape 23 protruding from the end edge 10c of the packaging member 10 is adhered to the underlying outer face 10b of the packaging member 10. Thus, the package 1 in the form of FIG. 2 is completed.

When the package 1 is to be unsealed, the tab tape 23 is first peeled off, and the end edge 10c is then pulled up to peel the fused faces of the packaging member 10 from each other, at the sealed portions 25 and 25. As the packaging member 10 is developed, the second release sheet 22 is peeled off from the pressure-sensitive adhesive layers 7 on the wing portions 2a. Then, the sanitary napkin 2 is separated from the packaging member 10 by peeling the first release sheet 21 from the pressure-sensitive adhesive layer 6 on the main body of the sanitary napkin 2.

The inner face 10a of the packaging member 10 is formed of the inner face layer 12 of the spun-bonded nonwoven fabric. Therefore, the release sheets 21 and 22 are firmly adhered to the surface of the inner face layer 12, so that the release sheets 21 and 22 are prevented from being separated from the packaging member 10 by the peeling forces for peeling the pressure-sensitive adhesive layers 6 and 7 of the sanitary napkin from the release sheets 21 and 22.

When the adhesive portion 23b of the tap tape 23 is peeled from the outer face lob of the packaging member 10, the spun-bonded nonwoven fabric forming the outer face 10b of the packaging member 10 is hardly fluffed. Therefore, the fibers hardly drop off and stick to the pressure-sensitive adhesive layer of the adhesive portion 23 so that the adhesion (or tack) of the pressure-sensitive adhesive layer do not drop seriously. Moreover, the partially heat-fused portions 15 are formed on the surface of the packaging member 10, and the adhesive portion 23b of the tab tape 23 is adhered to an area containing the partially heat-fused portions 15. Therefore, the adhesion (or tack) strength is high, and the fibers in the surface of the packaging member 10 are prevented from dropping and sticking to the pressure-sensitive adhesive layer of the adhesive portion 23b.

When the adhesive portion 23b of the tab tape 23 is adhered to the outer face 10b of the packaging member 10, moreover, the release sheet 22 exists under the adhesive portion 23b. Therefore, this release sheet 22 stabilizes the portion of the packaging member 10, to which the adhesive portion 23b of the tab tape 23 are adhered, so that adhesive portion 23b of the tab tape 23 is reliably adhered to the outer face 10b when the package is to be formed. This is also true for wrapping a used sanitary napkin in the packaging member 10 after sealed.

When the fuse faces of the packaging members 10 are to be peeled from each other at the sealed portions 25 and 25 for the unsealing purposes and when the used sanitary napkin is to be wrapped in the packaging member 10, moreover, the packaging member 10 hardly causes zipping sound such as rustling sound.

Furthermore, with the high rigidity region being thus formed by providing the release sheets 21 and 22 at the center of the packaging member 10, the packaging member 10 is excellent in shape retaining properties as a whole so that it is prevented from being unintentionally curled or folded. Therefore, the packaging member 10 hardly comes into direct contact with the pressure-sensitive adhesive layers of the sanitary napkin (in either case of unsealing the package or wrapping it after use) to improve handleability. Even if the sanitary napkin contacts at its pressure-sensitive adhesive layers with the inner face 10a or the outer face 10b of the packaging member 10, on the other hand, what contacts is the surface of the spun-bonded nonwoven fabric so that the packaging member 10 and the pressure-sensitive adhesive layers are easily separated. In addition, the fibers hardly drop and stick to the pressure-sensitive adhesive layers so that the adhesion (or tack) of the pressure-sensitive adhesive layers is not lowered.

EXAMPLE

The intermediate layer 11 was formed of a melt-blown nonwoven fabric having a basis weight of 3 g/m$^2$ and composed of PP fibers of a fineness of 0.44 dtex. The inner face layer 12 and the outer face layer 13 were formed of a spun-bonded nonwoven fabric having a basis weight of 7 g/m$^2$ and composed of continuous fibers of PP of a fineness of 2.2 dtex. These three layers were laminated and heated by heat emboss rollers to form the partially heat-fused portions 15 having an area ratio of 16% (i.e., 16% of the entire surface of the laminate was heat-fused) thereby to provide the packaging member 10 of Example. The total basis weight was 17 g/m$^2$.

(Comparison 1)

A spun-bonded nonwoven fabric having a basis weight of 20 g/m$^2$ and composed of continuous fibers of PP of a fineness of 2.2 dtex was formed as Comparison b 1.

<Water Resistance and Breathability Resistance>

Example and Comparison 1 were measured in water resistance according to JIS L-1092. The water resistance of Example was 135.2 mmH$_2$O; and the water resistance of Comparison 1 was 56.7 mmH$_2$O.

Example and Comparison 1 were also measured in breathability resistance by the breathability resistance tester manufactured by Kato Tech. The breathability resistance of Example was 0.054 kPa-s/m; and the breathability resistance of Comparison 1 was 0.038 kPa-s/m.

(Comparison 2)

A polyethylene resin, as prepared by blending 55% by weight of LLDPE (linear low density polyethylene) and 45% by weight of LDPE (low density polyethylene), was cast to form a film having a basis weight of 22 g/m$^2$ as Comparison 2.

<Zipping Sound>

Sanitary napkins were packaged with Example and Comparison 2, respectively, to prepare packages in the same form as that of the packages 1 of FIG. 2. The packages were fed between a roll having protrusions of 0.5 square millimeter (the area ratio of the protrusions to the roll surface was 40%) and a smooth roll, and were heat-sealed at their side edge regions at a temperature of 100° C. and under a pressure of 1960 kPa for 3 seconds, to thereby form heat-sealed portions.

The sound at the time when the heat-sealed portions were peeled off to unseal the package was measured by the microphone of a precise sound level meter at a distance of 30 cm. The sound was 55 dB(A) for Example and 86.1 dB(A) for Comparison 2.

<Tensile Strength>

When measured by using a tensile tester at a chuck distance of 100 mm and at a stress rate of 100 mm/min, the tensile strength (or the breaking strength) of Example was 16 N/25 mm in MD (i.e., the longitudinal direction) and 11.4 N/25 mm in CD (i.e., the transverse direction).

As has been described hereinbefore, the package of the invention can prevent large rustling sound when the packaging member is unsealed, while enhancing the effect of preventing dust or moisture from being infiltrated into the package. Moreover, the packaging member has a high surface strength.

Although the exemplary embodiment has been shown and described, the invention is not limited to the embodiment shown. Therefore, the scope of the invention is intended to be limited solely by the scope of the claims that follow.

What is claimed is:

1. A package comprising
   an absorbent articles; and
   a packaging member, the absorbent article including:
   a back sheet; a liquid-permeable top sheet; and an absorbent layer sandwiched between the back sheet and the top sheet, and being folded and packaged with the packaging member, confronting faces of each side edge region of the packaging member being joined to each other outside of the absorbent article,
   wherein the packaging member is formed of a nonwoven fabric composed of thermoplastic fibers, the nonwoven fabric having a plurality of heat-fused portions arranged thereon in a predetermined pattern, the heat-fused portions being formed by pressing and heat-fusing the nonwoven fabric,
   wherein the nonwoven fabric has a tensile strength of from 4.5 to 20 N/25 mm in MD and from 4.5 to 15 N/25 mm in CD and has a breathability resistance of at least 0.04 kPa-s/m.

2. The package as set forth in claim 1,
   wherein each heat-fused portion has an area of from 0.07 to 0.28 mm$^2$, and the area ratio of the heat-fused portions to the packaging member is from 10 to 30%.

3. The package as set forth in claim 1, wherein a water resistance of the packaging member is at least 80 mmH$_2$O according to JIS L-1092 (Method A: a low water pressure method).

4. The package as set forth in claim 1,
   wherein a bending resistance of the packaging member is from 30 to 70 mm at an average value of MD and CD according to JIS L-1018 (a cantilever method).

5. The package as set forth in claim 1,
   wherein a pressure-sensitive adhesive layer is disposed on the back sheet of the absorbent article, and a release sheet, to which the pressure-sensitive adhesive layer is to be adhered, is fixed on an inner face of the packaging member, at a portion to confront the back sheet of the absorbent article.

6. The package as set forth in claim 5,
   wherein a bending resistance of the release sheet is from 50 to 120 mm at an average value of MD and CD according to JIS L-1018 (a cantilever method).

7. The package as set forth in claim 1,
   wherein the packaging member is folded together with the absorbent article to have two portions, one overlying the other, an overlying portion has one end edge of the packaging member which is not directly joined to an underlying portion, wherein a tab tape is fixed on an outer face of the overlying portion of the packaging member, and has a portion protruding from the end edge, the portion protruding being provided with a pressure-sensitive adhesive layer which is adhered to an outer face of the underlying portion of the packaging member.

8. The package as set forth in claim 7, wherein the region to which the pressure-sensitive adhesive layer of the tab tape is adhered, contains the heat-fused portions.

9. A package comprising an absorbent article; and a packaging member having a breathability resistance of at least 0.04 kPa-s/m, the absorbent article including:
a back sheet; a liquid-permeable top sheet; and an absorbent layer sandwiched between the back sheet and the top sheet, and being folded and packaged with the packaging member, confronting faces of each side edge region of the packaging member being joined to each other outside of the absorbent article, wherein the packaging member includes: an inner face layer confronting the back sheet of the absorbent article; an outer face layer directed outward of the package; and an intermediate layer sandwiched between the inner face layer and the outer face layer, the intermediate layer being formed of a melt-blown nonwoven fabric composed of thermoplastic micro fibers, the inner face layer and the outer face layer being formed of a spun-bonded nonwoven fabric composed of continuous thermoplastic filaments, wherein the inner face layer, the intermediate layer and the outer face layer are heat-fused to one another.

10. The package as set forth in claim 9, wherein the water resistance of the packaging member is at least 80 mmH$_2$O according to JIS L-1092 (Method A: a low water pressure method).

11. The package as set forth in claim 9, wherein the packaging member is folded together with the absorbent article to have two portions, one overlying the other, an overlying portion has one end edge of the packaging member which is not directly joined to an underlying portion, wherein a tab tape is fixed on an outer face of the overlying portion of the packaging member, and has a portion protruding from the end edge, the portion protruding being provided with a pressure-sensitive adhesive layer which is adhered to an outer face of the underlying portion of the packaging member.

12. A package comprising an absorbent article; and a packaging member having a plurality of heat-fused portions arranged thereon in a predetermined pattern, the heat-fused portions being formed by pressing and heat-fusing the inner face layer, the intermediate layer and the outer face layer, the absorbent article including:
a back sheet; a liquid-permeable top sheet; and an absorbent layer sandwiched between the back sheet and the top sheet, and being folded and packaged with the packaging member, confronting faces of each side edge region of the packaging member being joined to each other outside of the absorbent article, wherein the packaging member includes: an inner face layer confronting the back sheet of the absorbent article; an outer face layer directed outward of the package; and an intermediate layer sandwiched between the inner face layer and the outer face layer, the intermediate layer being formed of a melt-blown nonwoven fabric composed of thermoplastic micro fibers, the inner face layer and the outer face layer being formed of a spun-bonded nonwoven fabric composed of continuous thermoplastic filaments, wherein the inner face layer, the intermediate layer and the outer face layer are heat-fused to one another, and wherein each heat-fused portion has an area of from 0.07 to 0.28 mm$^2$, and the area ratio of the heat-fused portions to the packaging member is from 10 to 30%.

13. The package as set forth in claim 12, wherein the packaging member is folded together with the absorbent article to have two portions, one overlying the other, an overlying portion has one end edge of the packaging member which is not directly joined to an underlying portion, wherein a tab tape is fixed on an outer face of the overlying portion of the packaging member, and has a portion protruding from the end edge, the portion protruding being provided with a pressure-sensitive adhesive layer which is adhered to an outer face of the underlying portion of the packaging member, wherein the region to which the pressure-sensitive adhesive layer of the tab tape is adhered, contains the heat-fused portions.

14. A package comprising an absorbent article; and a packaging member having a bending resistance of 30 to 70 mm at an average value of MD and CD according to JIS L-1018 (a cantilever method), the absorbent article including:
a back sheet; a liquid-permeable top sheet; and an absorbent layer sandwiched between the back sheet and the top sheet, and being folded and packaged with the packaging member, confronting faces of each side edge region of the packaging member being joined to each other outside of the absorbent article, wherein the packaging member includes: an inner face layer confronting the back sheet of the absorbent article; an outer face layer directed outward of the package; and an intermediate layer sandwiched between the inner face layer and the outer face layer, the intermediate layer being formed of a melt-blown nonwoven fabric composed of thermoplastic micro fibers, the inner face layer and the outer face layer being formed of a spun-bonded nonwoven fabric composed of continuous thermoplastic filaments, wherein the inner face layer, the intermediate layer and the outer face layer are heat-fused to one another.

15. A package comprising an absorbent article; and a packaging member, the absorbent article including:
a back sheet; a liquid-permeable top sheet; and an absorbent layer sandwiched between the back sheet and the top sheet, and being folded and packaged with the packaging member, confronting faces of each side edge region of the packaging member being joined to each other outside of the absorbent article, wherein the packaging member includes: an inner face layer confronting the back sheet of the absorbent article; an outer face layer directed outward of the package; and an intermediate layer sandwiched between the inner face layer and the outer face layer, the intermediate layer being formed of a melt-blown nonwoven fabric composed of thermoplastic micro fibers, the inner face layer and the outer face layer being formed of a spun-bonded nonwoven fabric composed of continuous thermoplastic filaments, wherein the inner face layer, the intermediate layer and the outer face layer are heat-fused to one another, wherein a pressure-sensitive adhesive layer is disposed on the back sheet of the absorbent article, and a release sheet having a bending resistance of from 50 to 120 mm at an average value of MD and CD according to JIS L-1018 (a cantilever method), to which the pressure-sensitive adhesive layer is to be adhered, is fixed on an inner face of the packaging member, at a portion to confront the back sheet of the absorbent article.

* * * * *